United States Patent [19]

Mattox

[11] Patent Number: 5,198,455
[45] Date of Patent: Mar. 30, 1993

[54] ORGANIC STABILIZERS

[75] Inventor: John R. Mattox, Perkasie, Pa.

[73] Assignee: Rohm and Haas Company, Philadelphia, Pa.

[21] Appl. No.: 292,681

[22] Filed: Jan. 3, 1989

[51] Int. Cl.$^5$ .................. A61K 31/425; C07D 275/02
[52] U.S. Cl. .................... 514/372; 548/212; 162/161; 504/156
[58] Field of Search ............ 548/213; 71/67; 514/372; 162/161

[56] References Cited

U.S. PATENT DOCUMENTS

| | | | |
|---|---|---|---|
| 3,523,121 | 9/1970 | Lewis et al. | 260/302 |
| 3,761,488 | 9/1973 | Lewis et al. | 260/302 |
| 4,129,448 | 9/1978 | Greenfield et al. | 106/15 R |
| 4,165,318 | 8/1979 | Greenfield et al. | 260/302 A |
| 4,241,080 | 12/1980 | Burk et al. | |
| 4,539,071 | 9/1985 | Clifford et al. | 514/372 |

FOREIGN PATENT DOCUMENTS 194146 8/1986 European Pat. Off. .
1318306 3/1983 Japan .

*Primary Examiner*—Jane T. Fan
*Assistant Examiner*—Celia Chang
*Attorney, Agent, or Firm*—Michael B. Fein

[57] ABSTRACT

Organic stabilizers are used to stabilize various materials which are normally unstable neat or in solution. These compositions exhibit bactericidal, fungicidal and algaecidal properties.

7 Claims, No Drawings

ORGANIC STABILIZERS

This invention relates to stable compositions of 3-isothiazolones, their preparation, and their use in controlling living organisms. The isothiazolones which are stabilized include those disclosed in U.S. Pat. Nos. 3,523,121 and 3,761,488 as represented by the following structural formula:

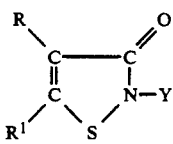

IA wherein

Y is an unsubstituted or substituted alkyl of from 1 to 18 carbon atoms, an unsubstituted or halo substituted alkenyl or alkynyl of from 2 to 8 carbon atoms, and, preferably, from 2 to 4 carbon atoms, an unsubstituted or substituted cycloalkyl of from 5 to 8 carbon atoms, an unsubstituted or substituted aralkyl or an unsubstituted or substituted aryl;

R is hydrogen, halo, or a ($C_1$-$C_4$)alkyl and $R^1$ is hydrogen, halo or ($C_1$-$C_4$)alkyl.

Representative Y substituents include methyl, ethyl, propyl, isopropyl, butyl, hexyl, octyl, cyclohexyl, benzyl, 3,4-dichlorobenzyl, 4-methoxybenzyl, 4-chlorobenzyl, 3,4-dichlorophenyl, 4-methoxyphenyl, hydroxymethyl, chloromethyl, chloropropyl and the like.

Preferred isothiazolones are 5-chloro-2-methyl-3-isothiazolone, 2-methyl-3-isothiazolone, 2-octyl-3-isothiazolone, 4,5-dichloro-2-cyclohexyl-3-isothiazolone and 4,5-dichloro-2-octyl-3-isothiazolone.

Japanese Patent 12243/83 discloses stabilizing a mixture of an isothiazolone and 2-hydroxymethyl-2-nitro-1,3-propanediol with a diol solvent. However, 2-hydroxymethyl-2-nitro-1,3-propanediol is a formaldehyde releaser, which is known to stabilize isothiazolones (see U.S. Pat. Nos. 4,165,318 and 4,129,448).

European Patent Application 194,146 discloses stabilizing isothiazolones in non-aqueous, salt-free systems by several hydroxylic solvents, outstanding among them dipropylene glycol.

A series of patents to Burk et al. teaches stabilization of halogenated amide antimicrobials, such as 2,2-dibromonitrilopropionamide, usually in the presence of some water, with a variety of organic stabilizers. U.S. Pat. No. 4,241,080 teaches acid or anhydride stabilizers. There is no suggestion that any of these stabilizers would be useful in the neat or non-aqueous stabilization of isothiazolones.

Thus, until now means for stabilization of isothiazolones against thermal degradation or storage degradation has generally been by metal salts, formaldehyde or formaldehyde releasers.

Both formaldehyde or formaldehyde-releasers and salt stabilization of isothiazolones have some drawbacks. Formaldehyde is a suspected carcinogen, and it is desirable not to use formaldehyde in applications where contact with human skin or lungs may occur.

This invention is directed to stable biocidal isothiazolone compositions in which (1) water is substantially eliminated, (2) salt neutralization is eliminated and (3) the need for nitrate stabilizer salts is substantially eliminated. Such stabilization is accomplished by the addition of organic anhydrides.

The anhydrides of this invention (I–IV, infra) are those having the following general formulas:

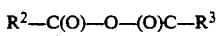

where $R^2$ and $R^3$ are the same or different radical selected from alkyl, cycloalkyl, aryl, alkylaryl, arylalkyl, and —C(O)—OR$^4$, and where $R^4$ is hydrogen, alkyl, cycloalkyl, aryl, alkylaryl, or arylalkyl;

II where X is $CR^5{=}CR^6$, $CR^5R^6{-}CR^5{=}CR^6$, or $(CR^5R^6)_n$, where n is 2 or 3, and where $R^5$ and $R^6$ are the same or different are chosen from the class of $R^2$, $R^3$, H or Cl;

III where Z completes a 4, 5, 6 or 7-membered saturated, unsaturated, or heterocyclic ring, and may be substituted with one or more $R^5$ or $R^6$ groups;

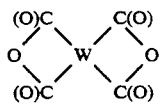

where W is an aromatic nucleus.

This invention comprises a composition which contains from about 0.1 to about 99.9 parts of one or more isothiazolones and an effective amount of an anhydride of Formulas I to IV (supra), preferably, an anhydride in the range of from 0.1 to about 99.9 percent.

More preferably, the composition comprises at least one isothiazolone wherein Y is $C_1$–$C_{18}$ alkyl or $C_3$–$C_{12}$ cycloalkyl; R is hydrogen or halo; and $R^1$ is hydrogen or halo. Typical formulation ranges are illustrated in the following Table (all percentages are parts by weight) for both a concentrated solution of the isothiazolone and a dilute solution. For certain uses, such as shipping of large quantities, more concentrated solutions may also be utilized. In certain instances, where the anhydride is a solid at temperatures which might be reached in storage, such as about 55° or above, it may be desirable to co-blend the isothiazolone and the anhydride in a solid mixture. Such anhydrides as maleic (mp. 60° C.), succinic anhydride (mp. 120° C.) and phthalic anhydride (mp. 132° C.) may be utilized.

TABLE

| | FORMULATIONS | |
|---|---|---|
| Isothiazolone (IA, Supra) | anhydride (I-IV, supra) | Solvent |
| 0.1–99.9% | 0.1%–99.9% | 0–99.8% |
| | Preferred | |
| 1–50% | 1–25% | 25–98% |
| | More Preferred | |
| 1–25% | 1–10% | 65–98% |

When it is desired to package the isothiazolone with only the stabilizer and no other organic solvent or water present the amount of stabilizer or mixture of stabilizers employed will be from about 1 percent to about 25 percent. The isothiazolone may be present in a bulk form or packaged or encapsulated in some manner, including a form for controlled release. The ratio of anhydride to isothiazolone is preferably from about 1:7 to about 1.5:1.

Solvents other than anhydrides may be used to dissolve the isothiazolones and may be any organic solvent which dissolves the isothiazolones, are compatible with the proposed end use, do not destabilize the isothiazolone, and do not react with the anhydride to eliminate its stabilizing action. For this reason, hydroxylic solvents, for example, polyols, such as glycols, alcohols and the like, are less preferred.

In certain formulations, hydrocarbons, either aliphatic or aromatic, are useful solvents.

Preferred solvents are capped polyols, wherein the free hydroxy is replaced with an ether or ester function. Especially preferred are 2,5,8,11-tetraoxadecane, commonly known as triethylene glycol dimethyl ether or triglyme, and 4,7-dioxaundecanol-1 acetate, commonly known as diethylene glycol butyl ether acetate.

The amounts of anhydride employed will vary depending on use conditions and concentrations of the isothiazolone in the mixture. In more concentrated solutions, effective amounts of anhydride based on isothiazolone are in the ratios of from about 1:4 to about 1:2. Obviously higher amounts may be used, but at additional cost. At low levels of dilution of the isothiazolone (such as from 1 to 2 percent isothiazolone in the solvent), the ratio of stabilizer to isothiazolone can range from about 1:7 to about 2:1.

This invention permits the stabilization of isothiazolones wherein the previously necessary stabilization salts are substantially reduced and even eliminated. Useful stabilization salts which can be employed are those disclosed in U.S. Pat. Nos. 3,870,795 and 4,067,878 and include stabilization salts selected from:

1) Metal nitrates, where the metal is barium, cadmium, calcium, chromium, cobalt, copper, iron, lead, lithium, magnesium, manganese, mercury, nickel, sodium, silver, strontium, tin, zinc and the like; and 2) Copper (2+) salts where the anion is halide, sulfate, nitrate, nitrite, acetate, chlorate, perchlorate, bisulfate, bicarbonate, oxalate, maleate, carbonate, or phosphate and the like.

Uses of these new organically stabilized biocides are typically at any locus subject to contamination by bacteria, fungi or algae. Typically loci are in aqueous systems such as water cooling, laundry wash water, oil systems such as cutting oils, oil fields and the like where microorganisms need to be killed or where their growth needs to be controlled.

The stabilized biocide compositions of this invention are advantageous over salt stabilized isothiazolones described in the art and are the biocides of choice where salts pose a problem. For example, certain emulsions upon the addition of a salt may coagulate. The compositions of this invention avoid this problem and therefore can be used in emulsions such as photographic emulsions, coating emulsions, (e.g. paints) to form solid protective or decorative films; electronic circuitry, wood, metals, plastics, fibers, membranes, carpet backings, ceramics and the like where surfaces need to be coated or protected, adhesives, caulks, and sensitive emulsions.

In many salt stabilized biocide systems of the prior art there is a potential for solids formation caused by interactions with other salts in the system, interaction with certain salt forming organics, by the conversion to organic salts, or simply by incompatibility with the system. The stabilized biocide compositions of this invention would be preferred in those systems. Also, the compositions of this invention are useful in fuel systems such as diesel fuel, gasoline, kerosene, certain alcohols, and the like, because they eliminate the possibility of salt deposits on component parts. Another reason for eliminating salts is to avoid an environment in which corrosion can occur. For example, chloride salts (among others) have a corrosive effect on many metals and are to be avoided where possible. In water treatment systems where low cation and anion levels are important, this is especially true. Those familiar with the art in various areas where biological growth needs to be controlled will quickly recognize those applications where significant reduction of or elimination of salts will be desired. In many cases it is necessary to eliminate interactions between the stabilizing salts and other components of the system or formulation components which otherwise could reduce the performance or value of such systems.

It is also recognized that the isothiazolone stabilizers of this invention have other applications known to those skilled in the art. For example, anhydrides are known to serve as reactive scavengers for molecules containing —OH, —NH$_2$, —SH and other nucleophilic groups. A biocide formulation stabilized with an anhydride would be particularly advantageous where the dual function of biocidal/biostatic activity and scavenging would lead to advantageous results.

Because isothiazolone biocides are so active, the low level required to achieve stabilization also makes them ideal when compared to many known biocides because at the low levels required they are not likely to interfere with other components in systems requiring protection or with systems upon which the protected systems will be applied.

Potential areas of general application include disinfectants, sanitizers, cleaners, deodorizers, liquid and powder soaps, skin removers, oil and grease removers, food processing chemicals, dairy chemicals, food preservatives, animal food preservatives, wood preservation, paint, lazures, stains, mildewcides, hospital and medical antiseptics, metal working fluids, cooling water, air washers, petroleum production, paper treatment, paper mill slimicides, petroleum products, adhesives, textiles, pigment slurries, latexes, leather and hide treatment, petroleum fuel, laundry sanitizers, agricultural formulations, inks, mining, nonwoven fabrics, petroleum storage, rubber, sugar processing, tobacco, swimming pools, cosmetics, toiletries, pharmaceuticals, chemical toilets, household laundry products, diesel fuel additives, waxes and polishes and many other applications where water and organic materials come in contact under conditions which allow the growth of undesired microorganisms.

In the stabilization of plastic articles, it is desirable to eliminate salts in the isothiazolones, as salts may contribute to deterioration of optical properties and/or increase water pickup and haze levels.

In some cosmetic formulations, it is also important to have low water and salt content. Eliminating nitrate salts avoids the possibility of nitrosamine formation with any amines present in the formulation. Removal of multivalent cations from the biocide may also eliminate the known possibility of creating physical incompatibility problems in certain cosmetic formulations caused by precipitation of salts or complexes.

It is known in the art that the performance of biocides can frequently be enhanced by combination with one or more other biocides. In fact, there have been numerous examples of synergistic combinations of biocides. Thus, other known biocides may be combined advantageously with the stabilized isothiazolones of this invention.

Isothiazolones are used as disinfectants, in oil field water treatment, as watercooling system microbiocides, as preservatives for aqueous dispersions or organic polymers, as wood pulp white water slimicides, as cosmetic preservatives, as cutting oil, jet fuel, and heating oil preservatives, and the like. Solutions of isothiazolones are also applied to a solid substrate, such as fabric, leather, or wood, as a preservative, or admixed with plastics.

The products of this invention are especially useful as preservatives for the following:

1. Cosmetics, as it eliminates or substantially reduces the presence of nitrates which under certain conditions in the presence of amines or amine precursors may lead to the formation of nitrosoamines.

2. Oils and fuels, since added salts and moisture are eliminated or minimized thus preventing potential corrosion, deposition or sludge formation.

3. Emulsions and dispersions that are sensitive to divalent cations are those contained in a wide variety of products, such as paints, cosmetics, floor polishes and binders.

4. Plastics, as it eliminates or substantially reduces precipitated salts which can contribute directly or indirectly to haze, opacity, or physical weakness in the surface.

The following examples will further illustrate this invention, but are not intended to limit it in any way. All parts and percentages are by weight and all temperatures in degrees Centigrade, unless otherwise stated.

For comparison of the stabilization of the compositions of this invention with known materials the following tests were employed: using a thermally-controlled solid metal block with bored holes as receptacles for the vials and with demonstrated temperature control, vials of stabilizer, solvent, and isothiazolone were made up and heated for fixed periods of time. The percentage of the starting isothiazolone remaining was determined high performance liquid chromatography (HPLC). Temperatures of 40° C., 55° C., and 70° C. were used. Results were considered indicative of acceptable stability when remainder values indicated essentially no loss during the time specified for the isothiazolone or isothiazolone mixture studied.

I. Stability Test for 5-Chloro-2-methylisothiazolin-3-one/2-Methylisothiazolin-3-one The 3:1 mixture of 5 chloro-2-methylisothiazolin-3-one/2-methylisothiazolin-3-one (16.2%) is mixed at 14% active ingredient (AI) in triglyme (76.8%) with the chosen stabilizer (7%). The retention of AI is measured after four weeks at 40° C. and after one and two weeks at 70° C. HPLC is used to measure AI. This is compared with a 3:1 mixture of 5-chloro-2-methylisothiazolin-3-one/2-methylisothiazolin-3-one stabilized with magnesium nitrate (15%).

The following results were obtained.

EXAMPLE 1

Stabilization Imparted by Organic anhydrides

| Stabilizer | 1 week, 70° | 2 weeks, 70° | 4 weeks, 40° |
|---|---|---|---|
| None | — | <10 | 32 |
| Mg(NO3)2, 15% | >85 | >85 | >85 |
| Acetic anhydride | 74 | 20 | 95 |
| Pivalic anhydride | 97 | 0 | 97 |
| Succinic anhydride | 0 | 0 | 76 |
| Maleic anhydride | 0 | — | 71 |
| Dichloromaleic anhydride | 72 | 30 | 101 |
| Glutaric anhydride | 12 | 0 | 64 |
| Tetrahydrofuran-maleic anhydride adduct | 0 | 0 | 11 |
| Pyromelletic anhydride | 4 | 0 | 85 |

EXAMPLE 2

Stability Results for Acetic Anhydride in Polar Solvents

Shown below is the percent of 5-chloro-2-methyl isothiazolin-3-one stabilized with acetic anhydride in various solvents remaining after 2 weeks at 70° C., where initial isothiazolone content was 14% and 7% stabilizer is used, the balance being the solvents listed. The second line is the control with no stabilizer. Under these fairly severe conditions, the anhydride appears to react with available hydroxide groups and be deactivated as a stabilizer.

| Tetra-Glyme | Dipropylene Glycol | Propylene Glycol Methyl Ether Acetate | Diethylene Glycol Butyl Ether Acetate | Triacetin (glyceryl triacetate) | Ethylene Glycol Diacetate | DPG + 5% Water |
|---|---|---|---|---|---|---|
| 27 | 0 | 44 | 49 | 15 | 8 | 0 |
| 0 | 0 | 0 | 17 | 21 | 0 | — |

EXAMPLE 3

Stabilization of Neat Mixture of 3:1 2-Methyl-5-Chloroisothiazolone and 2-Methylisothiazolone An admixture of the isothiazolones (no metal salt stabilizer) was prepared with 5% or 10% of the following stabilizers, stored at 40° C. for four weeks, and tested for active ingredient as in the previous examples.

| Stabilizer (S) | Retention of Activity | |
|---|---|---|
| | 5% S | 10% S |
| (Control) | 73.8 | 73.8 |
| Acetic anhydride | 84.3 | 82.3 |

EXAMPLE 4

Hair Shampoo

A solution containing 1.5% of N-methyl-5-chloroisothiazolin-3-one and N-methylisothiazolin-3-one (approximately 3:1 mixture) and 2.0% of pyromellitic anhydride stabilizer in 96.5 % dipropylene glycol diacetate is used as a preservative for a hair shampoo at 15 ppm AI.

EXAMPLE 5

Salt Shock of Emulsions

The advantage of eliminating salt shock in polymer emulsions is shown in the following example. Salt shock is observed as a precipitate or gelatinous mass that forms in the polymer emulsion when isothiazolone, containing stabilizers composed of divalent metal ions (e.g. $Mg++$, $Cu++$), is added as a preservative.

The polymer emulsion is initially passed through a 325 mesh screen to remove any gel that might be present from manufacture. Isothiazolone is added to a total amount of 30 ppm AI based on total polymer emulsion. A 250g. emulsion sample in a pint container is used. The sample is gently swirled after pipetting the appropriate amount of isothiazolone. The sample is inverted twice to mix and allowed to stand at ambient temperature for sixty minutes. The sample is again passed through a 325 mesh screen. Any gel or precipitate on the screen is washed with deionized water to remove residual, uncoagulated polymer emulsion. The material remaining on the screen is collected and dried overnight at 50° C. This is followed by heating 1 hour at 150° C. to remove any remaining water. The residue is then weighed. The amount of anhydride stabilizer is equal to that of the isothiazolone, and the solvent is butyl carbitol acetate.

The small amount of gel formed when the emulsion is preserved with salt-free anhydride-stabilized isothiazolone will not be detrimental in the use of the emulsion in various applications such as paints, caulks, and the like. The amount of gel formed when salt-stabilized isothiazolone is used as a preservative would be easily visible and objectionable.

EXAMPLE 6

Microbial Speed-of-Kill

The following test, when carried out to determine the microbial speed of kill of an anhydride stabilized isothiazolone compared to the nitrate stabilized isothiazolone, will illustrate equivalent bactericidal activity when either the nitrate or anhydride stabilizer is used.

The speed-of-kill test measures bactericidal activity in water free of organic matter. It measures the loss of cell viability in an aqueous suspension of bacterial cells as a function of time when these cells are contacted with a defined concentration of test compound in the water. This is done by taking aliquots of the cell suspensions at the appropriate time interval and assaying the number of viable cells per milliliter by plate count or most probable number (MPN) methodology. These measurements are done on the cell suspensions containing no test compound. The viable cell counts of the test and control samples are then compared to determine cell death.

The inoculum is prepared by growing the bacteria on a slant for 24 hours and then harvesting the cells into phosphate buffer. To start the test at zero time, one volume of bacterial inoculum is added to 100 volumes of test solution containing compound at the final test concentration. At appropriate time intervals, such as 2, 4 and/or 24 hours, aliquots of all the test samples and controls are assayed for viable cell count, reported as most probable number (MPN) per ml.

In this test, addition of anhydride stabilizer will not diminish the efficacy of a freshly prepared solution of a metal-salt-free isothiazolone in an organic solvent at either relatively high (14% AI) or relatively low (1.5%) isothiazolone concentrations. Comparisons are made against the unstabilized solution and against a metal-salt stabilized aqueous solution at the same AI level.

EXAMPLE 7

Minimum Inhibitory Content Testing

A minimum inhibitory concentration (MIC) test is used to evaluate the antimicrobial activity of a test compound in preservative applications. The MIC value is obtained in the following manner. A volume of the stock solution containing 1% AI is dispensed into enrichment broth to give an initial starting test concentration of 250 ppm compound. At the start of the test, each vessel in the dilution series, except the first vessel, contains an equal volume of the compound free broth. The first vessel contains twice the volume of broth with the starting concentration of test compound. One-half of the broth from the first vessel is transferred to the second vessel. After being mixed, one-half the resulting volume is removed from the second vessel and transferred to the third vessel. The entire cycle is repeated 8 to 12 times, depending on the number of dilutions desired. The result is a two-fold serial dilution of test compound in the enrichment broth.

Each vessel is then inoculated with a cell suspension of the appropriate test organism. Bacteria are grown in broth and fungi on agar slants, for a time and at a temperature appropriate to the species being tested. At the end of the growth period, the broth is vortexed to disperse the cells. In the case of fungi, the spores are harvested by pipetting water onto the slant and dislodging the spores with a sterile loop. The cell/spore suspensions are standardized by controlling incubation time and temperature and the volume of the diluent. Once inoculated, the vessels are incubated at the appropriate temperature, and then examined for growth/no growth. The minimum inhibitory concentration (MIC) is defined as the lowest concentration of compound that results in complete inhibition of growth of the test organism.

In this test, typical values for water-based salt stabilized systems are shown below. AI = Structure I 3 parts $(R^1=Cl, R=H, Y=CH_3)+1$ part $(R^1=R=H, Y=CH_3)$
System I: 14% AI in water, 15% magnesium nitrate.
System II: 1.5%AI in water, 1.6% $Mg(NO_3)_2$, 0.15% copper nitrate.

| Microorganism: | System I | System II |
| --- | --- | --- |
| Psfl = *Pseudomonas fluorescens* | 2 | 2 |
| Psal = *Pseudomonas aeruginosa* | 4 | 4 |
| Saur = *Staphylococcus aureus* | 16 | 16 |
| Ecol = *Escherichia coli* | 8 | 4 |
| Calb = *Candida albicans* | 2 | 2 |
| Anig = *Aspergillus niger* | 2 | 2 |
| Apul = *Aureobasidium pullulans* | 1 | 2/1 |

Values for freshly-prepared salt-free solutions at similar AI levels will be approximately those shown above, and those values will be essentially unaffected by presence of anhydride stabilizers of the present invention at use levels (relative to the AI concentration chosen) taught herein. Useful formulations are: 1.5% AI, 2% maleic anhydride, 96.5% diethylene glycol butyl ether acetate or 14% AI, 9% succinic anhydride, 77% propylene glycol methyl ether acetate.

What is claimed is:

1. A stabilized composition comprising
   (a) about 0.1 to 99.9 parts by weight of a compound of the formula

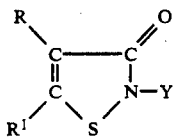

Ia wherein
   Y is selected from the group consisting of
   an unsubstituted alkyl group of one to 18 carbon atoms;
   a substituted alkyl group having at least one hydrogen atom replaced by hydroxy, halo, cyano, alkylamino, dialkylamino, phenylamino, halophenylamino, carboxy, carbalkoxy, alkoxy, acryloxy, morpholino, piperidino, pyrrolidonyl, carbamoxy, or isothiazolonyl, wherein the total number of carbon atoms in the substituted alkyl group does not exceed 18;
   an unsubstituted or halo-substituted alkenyl group of two to 18 carbon atoms;
   an unsubstituted or halo-substituted alkynyl group of two to 18 carbon atoms;
   an unsubstituted or alkyl-substituted cycloalkyl group having a three to six carbon atom ring and up to 12 carbon atoms;
   an unsubstituted or a halo-, lower alkyl-, or lower alkoxy-substituted aralkyl group wherein the total number of carbon atoms in the aralkyl group does not exceed 10 or;
   an unsubstituted or a halo-, nitro-, lower alkyl-, or lower carbalkoxy-, substituted aryl group wherein the total number of carbon atoms in the aryl group does not exceed 10; and
   R and $R^1$ are hydrogen, halo or alkyl,
   (b) about 0.1 to 99.9 parts by weight of an anhydride selected from the group consisting of acetic anhydride, pivalic anhydride, succinic anhydride, maleic anhydride, monochloromaleic anhydride, glutaric anhydride, phthalic anhydride, and pyromellitic anhydride; and
   0 to about 99.8% of an organic solvent
   wherein said composition is substantially free of water.

2. The composition of claim 1 which comprises from 0.1 to 99.9 parts of one or more compound of formula Ia; from 0.1 to 99.9 parts of said anhydride; and from 0 to 99.8% of an organic solvent.

3. The composition of claim 2 which comprises from 1 to 50 parts of the isothiazolones; from 1 to 25 parts of the anhydride and from 25 to 98 parts of said solvent.

4. The composition of claim 3 which comprises from 1 to 25 parts of the isothiazolone, from 1 to 10 parts of the anhydride and from 65 to 98 parts of said solvent.

5. The composition of claim 4 wherein Y is $C_1-C_{18}$ alkyl or $C_3-C_{12}$ cycloalkyl; R is hydrogen or halo and $R^1$ is hydrogen or halo.

6. The composition of claim 5 which comprises 14 parts of an isothiazolone selected from 5-chloro-2-methyl-3-isothiazolone, 2-methyl-3-isothiazolone, 2-octyl-3-isothiazolone, or 4,5-dichloro-2-octyl-3-isothiazolone.

7. The composition of claim 5 which comprises 1.5 parts of an isothiazolone selected from 5-chloro-2-methyl-3-isothiazolone, 2-methyl-3-isothiazolone, 2-octyl-3-isothiazolone, or 4,5-dichloro-2-octyl-3-isothiazolone.

* * * * *